(12) United States Patent
Benz

(10) Patent No.: US 6,716,362 B1
(45) Date of Patent: Apr. 6, 2004

(54) METHOD FOR THIN FILM LASER REFLECTANCE CORRELATION FOR SUBSTRATE ETCH ENDPOINT

(75) Inventor: Jason Michael Benz, Essex Junction, VT (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/695,028

(22) Filed: Oct. 24, 2000

(51) Int. Cl.[7] .............................................. H01L 21/301
(52) U.S. Cl. ............................ 216/12; 216/60; 216/85; 438/8; 438/9; 438/16
(58) Field of Search ............................. 216/12, 60, 85; 438/8, 9, 16

(56) References Cited

U.S. PATENT DOCUMENTS

| | | | | |
|---|---|---|---|---|
| 4,367,044 A | * | 1/1983 | Booth et al. | 356/504 |
| 4,717,446 A | * | 1/1988 | Nagy et al. | 438/14 |
| 4,767,495 A | * | 8/1988 | Nishioka | 156/345.25 |
| 4,927,485 A | * | 5/1990 | Cheng et al. | 156/345.25 |
| 5,023,188 A | * | 6/1991 | Tanaka | 438/8 |
| 5,335,113 A | * | 8/1994 | Jackson et al. | 283/72 |
| 5,372,673 A | * | 12/1994 | Stager et al. | 438/697 |
| 5,382,483 A | | 1/1995 | Young | 430/5 |
| 5,405,721 A | | 4/1995 | Pierrat | 430/5 |
| 5,465,859 A | * | 11/1995 | Chapple-Sokol et al. | 216/12 |
| 5,582,939 A | | 12/1996 | Pierrat | 430/5 |
| 5,667,700 A | * | 9/1997 | Rudigier et al. | 216/12 |
| 5,891,352 A | | 4/1999 | Litvak | 216/85 |
| 6,046,796 A | * | 4/2000 | Markle et al. | 216/60 |
| 6,110,624 A | * | 8/2000 | Hibbs et al. | 430/394 |
| 6,350,361 B1 | * | 2/2002 | Sexton et al. | 205/82 |
| 6,406,641 B1 | * | 6/2002 | Golzarian | 216/85 |
| 2002/0164829 A1 | * | 11/2002 | Otsubo et al. | 438/14 |

FOREIGN PATENT DOCUMENTS

| | | | | |
|---|---|---|---|---|
| JP | 61051925 A | * | 3/1986 | H01L/21/302 |
| JP | 01231324 A | * | 9/1989 | H01L/21/302 |
| JP | 06252105 A | * | 9/1994 | H01L/21/302 |

OTHER PUBLICATIONS

IBM Technical Disclosure Bulletin, "Etching End–Point–Detection Technique", vol. 29, No. 2, Jul. 1986, pp. 759–760.
E.G. Smith, IBM Technical Disclosure Bulletin, "Second and Third Layer Quartz Via Etch End Point Detect Program", vol. 19, No. 3, Aug. 1976, pp. 875–877.
A.S. Bergendahl, et al., "End–Point Detection Method For Mask Etching", pp. 2645–2646, 1984.
E. G. Coombs, "Missing Peak Algorithm Modification For Etch End–Point Detection", IBM Technical Bulletin, vol. 24, No. 11B, Apr. 1982, pp. 6036–6037.

* cited by examiner

Primary Examiner—Anita Alanko
(74) Attorney, Agent, or Firm—Richard M. Kotulak, Esq.; McGinn & Gibb, PLLC

(57) ABSTRACT

A method of etching a substrate, includes measuring a reflectance signal from a reflective material deposited on the substrate as the substrate is being etched, correlating the substrate etch rate to the reflectance signal from the reflective material, and using the etch relation between the substrate and the reflective material to determine the etch target.

39 Claims, 3 Drawing Sheets

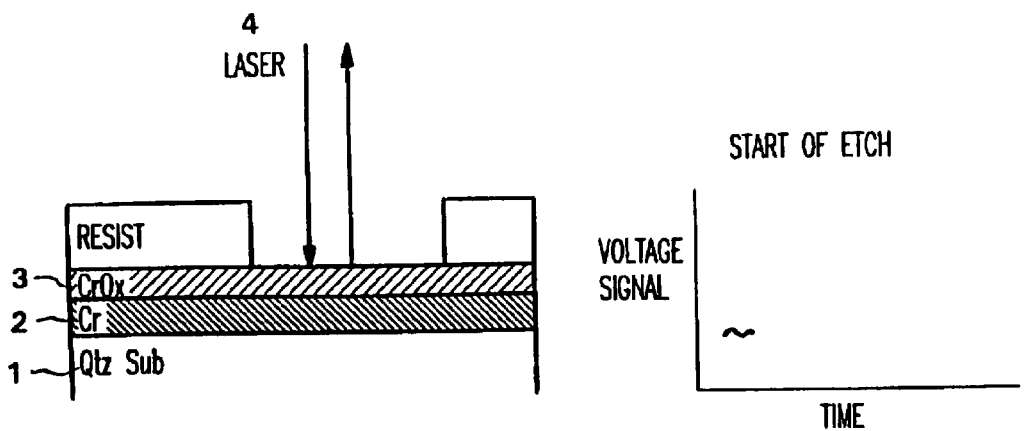
FIG.1A
Related Art
FIG.1B
Related Art
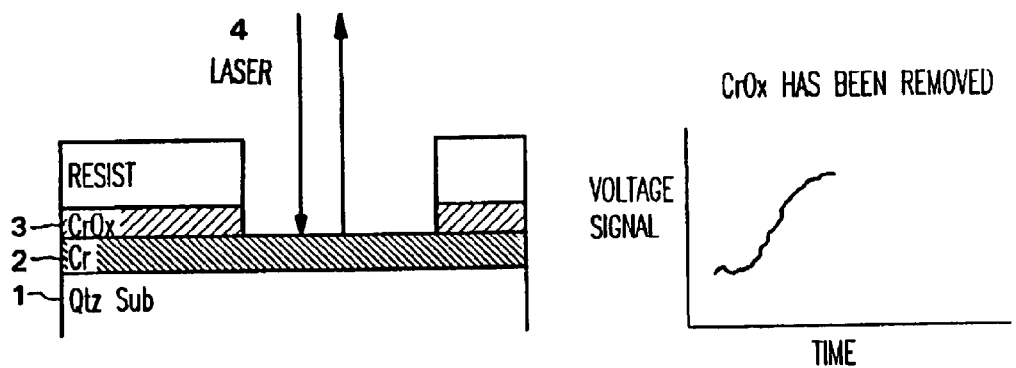
FIG.2A
Related Art
FIG.2B
Related Art
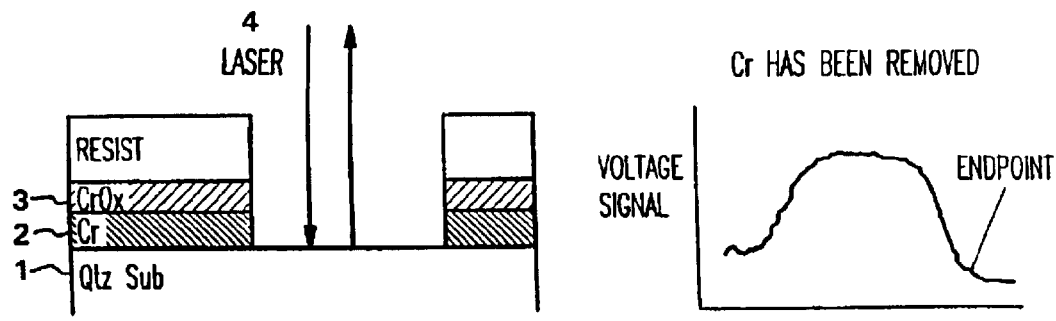
Related Art
FIG.3A
Related Art
FIG.3B

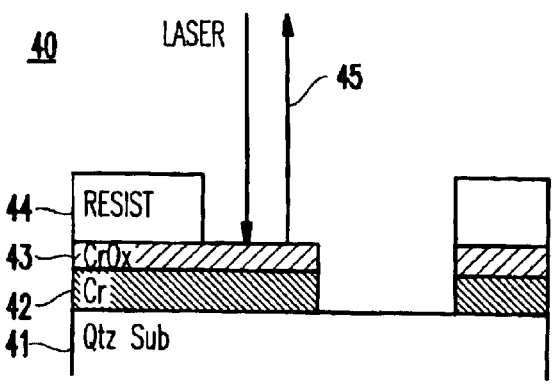
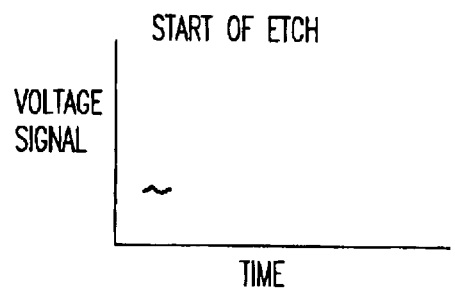
FIG.4A  FIG.4B
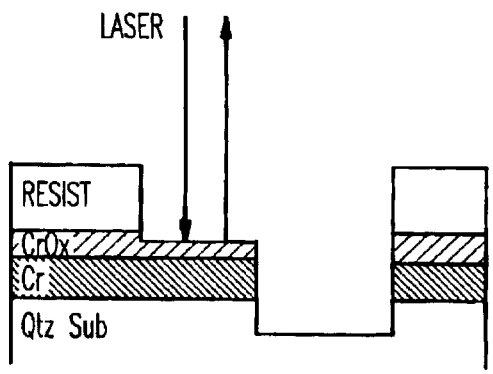
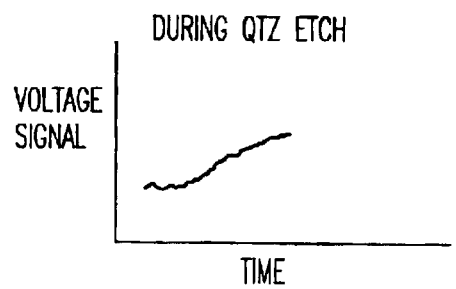
FIG.5A  FIG.5B
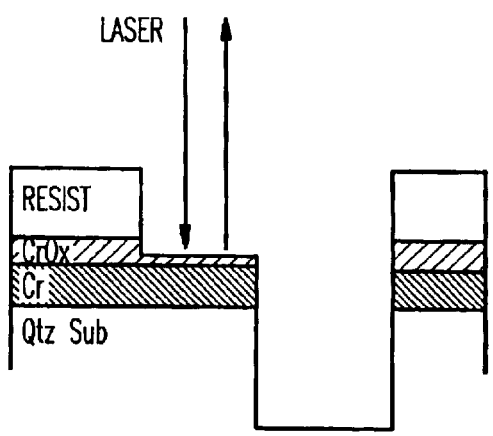
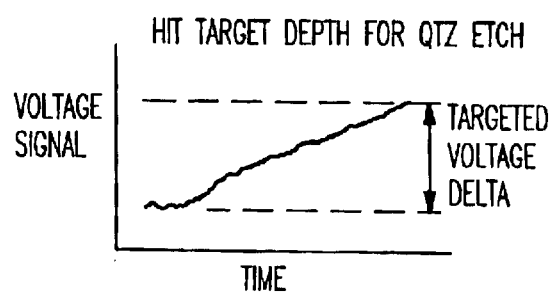
FIG.6A  FIG.6B

METHOD FOR THIN FILM LASER REFLECTANCE CORRELATION FOR SUBSTRATE ETCH ENDPOINT

BACKGROUND OF THE INVENTION

1. Field of the Invention

The present invention generally relates to endpoint detection, and more particularly to thin film laser reflectance correlation for quartz etch endpoint.

2. Description of the Related Art

Several conventional endpoint detection techniques exist in the industry for detecting the endpoint of substrates/materials such as quartz, etc. Examples include laser reflectance, optical emission spectroscopy, and mass spectroscopy. These techniques have been proven to work quite well for several plasma applications, etc. In each case, a change in either the film or the plasma, signals the endpoint of the film being etched.

However, these methods prove to be useless in the fabrication of alternating phase-shift masks because this particular process requires that portions of the photomask substrate (e.g., quartz) be etched to a specific depth. Since this involves etching into a bulk quartz substrate, where there is no etch stop, no change in either the film or plasma characteristics can be observed. This is a problem.

Previously, etching to the correct depth in quartz substrate was almost an art form, which also required some luck. The process, referred to as an "iterative etch process", would be typically performed as follows.

First, the operator assumes a quartz etch rate (e.g., based on the last run completed) and determines the time needed to etch about 80% of the desired depth. Next, the part is etched. Then, the part is unloaded and taken to a profilometer, where the approximate etch depth is measured. Etch rate is then re-calculated and then the part is loaded back into the etch tool to complete the remaining etch.

However, not only does this procedure require a lot of work, it also requires an extremely stable process.

Moreover, if the process etch rate fluctuates, the chances of "hitting" the correct depth drops dramatically. The procedure also demands a skilled operator, and several tool transfers, both of which are costly and not manufacturing-friendly.

Thus, these methods are very inaccurate and result in tedious, time-consuming operations requiring highly-skill, highly-trained operators. Otherwise, yield is low and waste of materials is high.

FIGS. 1A–3B illustrate the conventional etching process and the laser reflectance signal for the conventional dry etching of a chrome on glass etch.

In FIG. 1A, a substrate 1 (e.g., quartz) is shown having a chrome material 2 deposited thereon and a chromium oxide 3 is formed over the chrome 2. A laser 4 is shown for etching through the chromium oxide 3 (CrOx) to remove the chrome 2 on the substrate. A resist is shown for use as a patterning mask. FIG. 1B shows the voltage signal as a function of time at the start of etching to represent the reflectance of the laser.

FIGS. 2A and 2B respectively illustrate the etching of the CrOx and the associated waveform of the reflectance signal.

FIGS. 3A and 3B respectively illustrate the etching and removal of the Cr from the quartz substrate and the associated waveform of the reflectance signal until the endpoint is detected. As is evident, the reflectance signal changes as the etching continues.

Thus, FIGS. 1A–3B illustrate a typical laser reflectance trace used to etch chrome on the quartz substrate. This also represents typical methods used for endpointing on several types of dry etching processes, by simply changing the films involved, or the curve. The voltage signal could also be a wavelength signal emitted from the plasma (used in optical emission spectroscopy). In this particular case, in the conventional method, the laser is focused on the primary film (chrome). Since the chrome is reflective, and the substrate (quartz) below it is not reflective, by observing the laser reflectance voltage signal, which represents the amount of reflectivity, it is easy to judge when the chrome film has been completely etched. As the chrome oxide (CrOx), or anti-reflective layer, is quickly etched away the signal rises. At the peak of the signal, the chrome is exposed and begins to be etched away. When the chrome becomes thin, some of the signal is lost to transmission. Finally, when no chrome is remaining the signal flattens out due to the presence of the secondary film, quartz, which is transmissive.

Typical endpoint methods use software algorithms to detect a change in the output curve to trigger endpoint, as was done in the above example. However, as described above, the problem with etching quartz lies in the fact that there will be no change in the quartz film, or plasma to trigger an endpoint.

Typically, in alternating photomask production, a standard binary mask is used (e.g., chrome on a quartz substrate). As mentioned above, to etch the quartz substrate to a desired target depth, the iterative etch process is used. The idea behind this process is to etch to a pre-selected time. The etch depth is then measured to determine the etch rate. That calculated etch rate is then used to determine the etch time for the second etch pass. As mentioned above, this process has several problems including several tool in/outs (tool transfers leading to additional defects such as reduced yield), potential for operator error, increased defects, and it would be very susceptible to process variations. The use of an endpoint method would show tremendous benefits.

SUMMARY OF THE INVENTION

In view of the foregoing and other problems, drawbacks, and disadvantages of the conventional methods, an object of the present invention is to provide a method for thin film laser reflectance correlation.

In a first aspect, a method of etching a substrate according to the present invention includes measuring a reflectance signal from a reflective material deposited on the substrate as the substrate is being etched, correlating the substrate etch rate to the reflectance signal from the reflective material, and using the etch relation between the substrate and the reflective material to determine the etch target.

In a second aspect, a method of etching a material includes measuring a reflectance signal from a correlation material that is removed from the path of a second material that is to be etched as the second material is etched, correlating the second material etch rate to the reflectance signal from the correlation material, and using the etch ratio between the correlation material and the second material to determine the etch target.

In a third aspect, a method of etching a semiconductor substrate includes measuring a reflectance signal from an opaque material deposited on the semiconductor substrate as the semiconductor substrate is being etched, correlating the semiconductor substrate etch rate to the reflectance signal from the opaque material, and using the etch relation between the semiconductor substrate and the opaque material to determine the etch target.

Generally, the invention takes advantage of a metal film (e.g., a chrome film) which is already on a photomask used with the etching process. For purposes whereinbelow, chrome will be assumed to be the metal film, but of course, as would be known by one ordinarily skilled in the art after taking the present specification, any metal (or other opaque material) providing a predetermined reflectance signal could be used. The surface of the chrome film contains an anti-reflective chrome oxide which isolates the chrome from the etching process. This film is etched during the quartz etch process. By correlating the quartz etch to the rate of the chrome oxide etch, the reflectance signal from the chrome can be used to determine an endpoint for the quartz etch process.

With the unique and unobvious features of the invention, even if the process etch rate luctuates, the correct depth will still be etched. Further, a skilled operator is not required nor are the several tool transfers which are required by the conventional methods. Thus, a low-cost, efficient method is provided, thereby resulting in greater yield and less waste of materials.

BRIEF DESCRIPTION OF THE DRAWINGS

The foregoing and other objects, aspects and advantages will be better understood from the following detailed description of a preferred embodiment of the invention with reference to the drawings, in which:

FIGS. 1A–3B illustrate a conventional etching process and the laser reflectance signal for the conventional etching for chrome on glass dry etch;

FIGS. 4A–6B illustrates the inventive etching process and the laser reflectance signal for quartz dry etching (using CrOx as an exemplary material);

DETAILED DESCRIPTION OF A PREFERRED EMBODIMENT OF THE INVENTION

Figure 8:
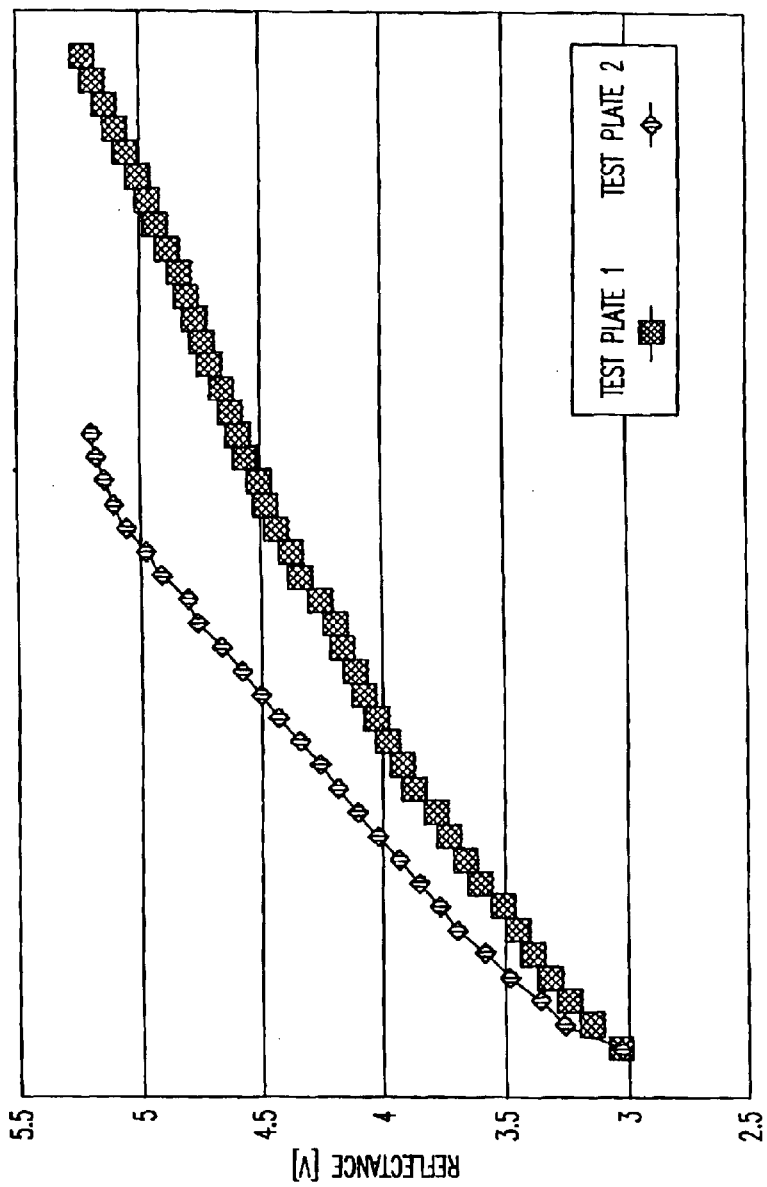
FIG. 8 illustrates a relationship of laser reflectance as a function of time for quartz endpoint.

Referring now to FIGS. 4A–8, the method of the present invention will be described hereinbelow.

Generally, the present invention takes advantage of the metal (e.g., chrome) film which is already on a photomask to be used with the present invention.

That is, the surface of the chrome film contains an anti-reflective chrome oxide. This film is attacked during the quartz etch. By correlating the quartz etch to the rate of the chrome oxide etch, the reflectance signal from the chrome can be used to determine an endpoint for the quartz. It is noted that, as mentioned above, other materials could be used for correlating their etch rate with the etching of the underlying substrate. Similarly, the substrate is not limited to quartz, but could be other materials such as silicon, Gallium Arsenide, or any deep trench etching application material.

Thus, knowing that the quartz etch process etches the chrome oxide as well, and knowing the behavior of the laser reflectance signal of the chrome oxide, as shown above, a potential endpoint method for etching quartz has emerged. The idea behind thin film laser reflectance correlation is to use a secondary film only to correlate, and trigger an endpoint on the primary film being etched.

In this particular case, the chrome film acts as the secondary film and the quartz substrate is of course the primary film, or the film being etched. Unlike other endpoint methods, the output being monitored for the endpoint detection is not physically representing the film being etched.

Referring now to the drawings, and more particularly to FIG. 4A, a structure 40 is shown for being etched. That is, structure 40 includes a substrate 41, a metal 42 (e.g., chrome) formed on the substrate 41, an oxide 43 (e.g., chrome oxide) formed on the metal 42, and a resist 44 for patterning the structure of interest. A laser 45 is shown for emitting a signal to the oxide 43 such that its reflectance can be measured. FIG. 4B illustrates the voltage signal as a function of time.

FIGS. 5A and 5B respectively illustrate the etching of the CrOx 43 and the associated waveform of the reflectance signal.

FIGS. 6A and 6B respectively illustrate the further etching and further removal of the metal (chrome) oxide from the substrate and the associated waveform of the reflectance signal as a function of voltage over time and the targeted voltage difference.

Figure 7:
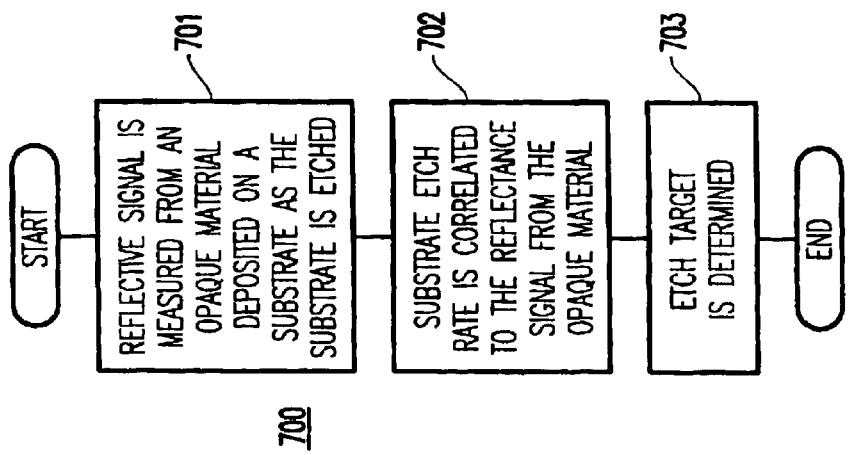
FIG. 7 is a flowchart of the inventive method 700 of etching a substrate and using laser reflectance correlation for etching endpoint detection.

For further ease of understanding, a flowchart of the inventive method 700 of etching a substrate, is shown in FIG. 7.

That is, in step 701, a reflectance signal is measured from an opaque material (e.g., such as metal or metal oxide, etc.) deposited on a substrate (e.g., quartz, silicon, etc.) as the. substrate is being etched.

In step 702, the substrate etch rate is correlated to the reflectance signal from the opaque material.

Finally, in step 703, by using the etch relation between the substrate and the opaque material, the etch target can be determined; In the exemplary application, a depth of the etch or some other characteristic of the etch target can be determined.

Thus, as evident from the above, a key difference between the invention and the conventional endpoint detection methods is that the output being monitored for endpoint detection is not physically representing the film being etched.

That is, by calculating the selectivity of the quartz substrate to the chrome oxide, the desired quartz etch depth can be translated into a chrome, or chrome oxide etch depth. Since the chrome oxide is not completely removed, the laser reflectance voltage climbs at a much slower, and linear pace. The laser reflectance voltage signal can then be targeted to specified chrome oxide depth. When a certain voltage delta has been observed, the etch process is discontinued. Assuming selectivity has remained constant, if the correct chrome oxide depth has been obtained then the quartz substrate should also be etched to the desired target.

The benefits of using this method include all the benefits of other endpoint methods used throughout the industry. The process is now less susceptible to process variations, operator error, and defects. Less tool in/outs saves on process time, as well as defects. This method also does not require any additional process steps, or equipment, and furthermore it takes advantage of the metal (chrome) film which is already in the process.

Two test plates were performed to determine the target signal to stop etching. Data from these plates is shown in FIG. 8.

As shown, the data suggests that the method works with reasonable repeatability, and within specifications. Each plate was etched with different processes. This shows that the method is effective across different process windows. The first plate shows a small endpoint site, whereas test plate 2 shows a larger endpoint site over chrome. Thus, a different test plate was used which effected the loading (etch rate). The plate was etched reasonably close to the targeted depth.

Hence, using the chrome for an endpoint signal solves many of the problems of the conventional methods. Use of an endpoint trace allows for better manufacturability. The skill of the operator is not as critical, and it allows for some process variations. Also, only one tool transfer (as opposed to three transfers as described above) is necessary.

A major advantage of this endpoint solution is that it requires no additional, or special processing. The inventive endpoint procedure can be inserted easily into the process flow, and makes the etch process more manufacturable than it is now. Further, the inventive method has improved turn-around-time, low cost, improved efficiency, and improved manufacturability.

While the invention has been described in terms of a preferred embodiment, those skilled in the art will recognize that the invention can be practiced with modification within the spirit and scope of the appended claims.

What is claimed is:

1. A method of etching a substrate, comprising:
   providing a substrate comprising a reflective material deposited on said substrate and a metal oxide deposited on said reflective material;
   etching said substrate to an etch target and etching said metal oxide;
   measuring a reflectance signal from said reflective material deposited on the substrate as the substrate is being etched;
   correlating a substrate etch rate to the reflectance signal from the reflective material; and
   using an etch relation between the substrate and the reflective material to determine the etch target,
   wherein the reflective material is isolated from the etching process,
   wherein the etch relation is determined by a ratio of etch rates between the metal oxide and the substrate, and
   wherein the etch target is determined before said metal oxide is completely removed.

2. The method of claim 1, wherein said substrate comprises quartz.

3. The method of claim 1, wherein said reflective material comprises metal.

4. The method of claim 3, wherein said metal comprises chrome.

5. The method of claim 3, wherein said metal is formed on a photomask for patterning said substrate.

6. The method of claim 3, wherein said metal has a metal oxide thereon, and wherein by correlating the substrate etch to the rate of the metal oxide etch, the reflectance signal from the metal is usable in determining an endpoint for the substrate etch.

7. The method of claim 1, wherein said reflective material comprises metal having said metal oxide thereon, and said substrate etch also etches said metal oxide on said metal, and wherein the reflectance correlation uses said metal as a secondary film only to correlate, and trigger an endpoint on the substrate as a primary film being etched,
   wherein an output being monitored for endpoint detection is not physically representing the primary film being etched.

8. The method of claim 3, wherein a surface of said metal contains an anti-reflective metal oxide, which is attacked during the substrate etch.

9. The method of claim 1, wherein said reflective material includes a metal having metal oxide formed thereon, and wherein an output being monitored for endpoint detection does not physically represent the film being etched, such that by calculating a selectivity of the substrate to the metal, a desired substrate etch depth is tanslatable into one of a metal etch and a metal oxide etch depth.

10. The method of claim 9, wherein the metal oxide is not completely removed, such that a waveform of the reflectance voltage climbs linearly and such that the reflectance voltage signal is targetable to a specified metal oxide depth.

11. The method of claim 9, wherein when a certain voltage difference is observed, the etch process is discontinued.

12. A method of etching a material, comprising:
    providing a substrate comprising a correlation material deposited on second material and a metal oxide deposited on said correlation material;
    etching said second material to an etch target and etching said metal oxide;
    measuring a reflectance signal from said correlation material that is removed from the path of the second material that is to be etched as the second material is etched;
    correlating the second material etch rate to the reflectance signal from the correlation material; and
    using an etch ratio between the correlation material and the second material to determine the etch target,
    wherein the correlation material is isolated from the etching process,
    wherein the etch ratio is determined by a ratio of etch rates between the metal oxide and the second material, and
    wherein the etch target is determined before the metal oxide is completely removed.

13. The method of claim 12, wherein said second material comprises quartz.

14. The method of claim 12, wherein said correlation material comprises metal.

15. The method of claim 14, wherein said metal comprises chrome.

16. The method of claim 14, wherein said metal is formed on a photomask for patterning said second material.

17. The method of claim 12, wherein said correlation material includes a metal oxide thereon, and wherein by correlating the second material etch to the rate of the metal oxide etch, the reflectance signal from the metal is usable in determining an endpoint for the substrate etch.

18. The method of claim 12, wherein said second material etch also etches said metal oxide on said metal, and wherein a thin film reflectance correlation uses said metal as a secondary film only to correlate, and trigger an endpoint on the second material as a primary film being etched,
    wherein an output being monitored for endpoint detection is not physically representing the primary film being etched.

19. The method of claim 14, wherein a surface of said metal contains an anti-reflective metal oxide, which is attacked during the second material etch.

20. The method of claim 12, wherein said correlation material includes a metal having metal oxide formed thereon, and wherein an output being monitored for endpoint detection does not physically represent the film being etched, such that by calculating a selectivity of the substrate to the metal, a desired second material etch depth is translatable into one of a metal etch and a metal oxide etch depth.

21. The method of claim 20, wherein the metal oxide is not completely removed, such that a waveform of the reflectance voltage climbs linearly and such that the reflectance voltage signal is targetable to a specified metal oxide depth.

22. The method of claim 12, wherein when a certain voltage difference is observed, the etch process is discontinued.

23. A method of etching a semiconductor substrate, comprising:

providing a semiconductor substrate comprising an opaque material deposited on said semiconductor substrate and a metal oxide deposited on said opaque material;

etching said semiconductor substrate to an etch target and etching said metal oxide;

measuring a reflectance signal from said opaque material deposited on the semiconductor substrate as the semiconductor substrate is being etched;

correlating the semiconductor substrate etch rate to the reflectance signal from the opaque material; and using an etch relation between the semiconductor substrate and the opaque material to determine the etch target, wherein the opaque material is isolated from the etching process, wherein the etch relation is determined by a ratio of etch rates between the metal oxide and the semiconductor substrate, and wherein the etch target is determined before the metal oxide is completely removed.

24. The method of claim 23, herein said semiconductor substrate comprises quartz.

25. The method of claim 23, wherein said opaque material comprises metal.

26. The method of claim 23, wherein said metal comprises chrome.

27. The method of claim 23, wherein said metal is formed on a photomask for pattering said substrate.

28. The method of claim 25, wherein said metal has a metal oxide thereon, and wherein by correlating the substrate etch to the rate of the metal oxide etch, the reflectance signal from the metal is usable in determining an endpoint for the substrate etch.

29. The method of claim 23, wherein said opaque material comprises metal having said metal oxide thereon, and said substrate etch also etches said metal oxide on said metal, and wherein the reflectance correlation uses said metal as a secondary film only to correlate, and trigger an endpoint on the substrate as a primary film being etched, wherein an output being monitored for endpoint detection is not physically representing the primary film being etched.

30. The method of claim 25, wherein a surface of said metal contains an anti-reflective metal oxide, which is attacked during the substrate etch.

31. The method of claim 8, wherein a reflectivity of said metal and a reflectivity of said anti-reflective metal oxide are different.

32. The method of claim 19, wherein a reflectivity of said metal and a reflectivity of said anti-reflective metal oxide are different.

33. The method of claim 30, wherein a reflectivity of said metal and a reflectivity of said anti-reflective metal oxide are different.

34. The method according to claim 1, wherein said etch relation comprises a correlation between the substrate etch and the reflectance signal.

35. The method according to claim 12, wherein said etch ratio comprises a correlation between the second material etch and the reflectance signal.

36. The method according to claim 23, wherein said etch ratio comprises a correlation between the second material etch and the reflectance signal.

37. The method of claim 1, wherein a change in a measurement of said reflectance signal is determined by a rate of said metal oxide etch.

38. The method of claim 12, wherein a change in a measurement of said reflectance signal is determined by a rate of said metal oxide etch.

39. The method of claim 23, wherein a change in a measurement of said reflectance signal is determined by a rate of said metal oxide etch.

* * * * *